(12) United States Patent
Bennett

(10) Patent No.: US 8,067,028 B2
(45) Date of Patent: Nov. 29, 2011

(54) DRUG DELIVERY DEVICE

(75) Inventor: Steven L. Bennett, Cheshire, CT (US)

(73) Assignee: Confluent Surgical Inc., Waltham, MA (US)

( * ) Notice: Subject to any disclaimer, the term of this patent is extended or adjusted under 35 U.S.C. 154(b) by 77 days.

(21) Appl. No.: 12/165,972

(22) Filed: Jul. 1, 2008

(65) Prior Publication Data

US 2009/0047349 A1 Feb. 19, 2009

Related U.S. Application Data

(60) Provisional application No. 60/964,488, filed on Aug. 13, 2007.

(51) Int. Cl.
*A61K 9/00* (2006.01)
*A61K 38/02* (2006.01)
*A61K 38/43* (2006.01)

(52) U.S. Cl. ........ 424/426; 424/486; 424/484; 424/94.1

(58) Field of Classification Search .................. None
See application file for complete search history.

(56) References Cited

U.S. PATENT DOCUMENTS

| | | |
|---|---|---|
| 2,533,004 A | 12/1950 | Ferry et al. |
| 3,520,949 A | 7/1970 | Shepard et al. |
| 4,101,380 A | 7/1978 | Rubinstein et al. |
| 4,359,049 A | 11/1982 | Redl et al. |
| 4,565,784 A | 1/1986 | Franzblau et al. |
| 4,601,286 A | 7/1986 | Kaufman |
| 4,631,055 A | 12/1986 | Redl et al. |
| 4,646,730 A | 3/1987 | Schonfeld et al. |
| 4,735,616 A | 4/1988 | Eibl et al. |
| 4,874,368 A | 10/1989 | Miller et al. |
| 4,902,281 A | 2/1990 | Avoy |
| 4,932,942 A | 6/1990 | Maslanka |
| 4,937,270 A | 6/1990 | Hamilton et al. |
| 4,938,763 A | 7/1990 | Dunn et al. |
| 4,938,763 A | 7/1990 | Dunn et al. |
| 4,978,336 A | 12/1990 | Capozzi et al. |
| 5,030,215 A | 7/1991 | Morse et al. |
| 5,041,292 A | 8/1991 | Feijen |
| 5,104,909 A | 4/1992 | Grasel et al. |
| 5,116,315 A | 5/1992 | Capozzi et al. |
| 5,143,662 A | 9/1992 | Chesterfield et al. |
| 5,162,430 A | 11/1992 | Rhee et al. |
| 5,192,743 A | 3/1993 | Hsu et al. |
| 5,219,564 A | 6/1993 | Zalipsky et al. |
| 5,290,776 A | 3/1994 | Caulkett et al. |
| 5,296,518 A | 3/1994 | Grasel et al. |
| 5,304,595 A | 4/1994 | Rhee et al. |
| 5,318,524 A | 6/1994 | Morse et al. |
| 5,324,775 A | 6/1994 | Rhee et al. |
| 5,328,955 A | 7/1994 | Rhee et al. |
| 5,368,563 A | 11/1994 | Lonneman et al. |
| 5,395,923 A | 3/1995 | Bui-Khac et al. |
| 5,399,351 A | 3/1995 | Leshchiner et al. |
| 5,405,607 A | 4/1995 | Epstein |
| 5,410,016 A | 4/1995 | Hubbell et al. |
| 5,413,791 A | 5/1995 | Rhee et al. |
| 5,419,491 A | 5/1995 | Breitsprecher |
| 5,426,148 A | 6/1995 | Tucker |
| 5,446,090 A | 8/1995 | Harris |
| 5,446,091 A | 8/1995 | Rhee et al. |
| 5,455,027 A | 10/1995 | Zalipsky et al. |
| 5,470,911 A | 11/1995 | Rhee et al. |
| 5,474,540 A | 12/1995 | Miller et al. |
| 5,475,052 A | 12/1995 | Rhee et al. |
| 5,476,909 A | 12/1995 | Kim et al. |
| 5,505,704 A | 4/1996 | Pawelka et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,550,187 A | 8/1996 | Rhee et al. |
| 5,550,188 A | 8/1996 | Rhee et al. |
| 5,565,519 A | 10/1996 | Rhee et al. |
| 5,567,435 A | 10/1996 | Hubbell et al. |
| 5,573,934 A | 11/1996 | Hubbell et al. |
| 5,583,114 A | 12/1996 | Barrows et al. |
| 5,605,541 A | 2/1997 | Holm |
| 5,614,587 A | 3/1997 | Rhee et al. |
| 5,626,863 A | 5/1997 | Hubbell et al. |
| 5,631,322 A | 5/1997 | Veronese et al. |
| 5,643,464 A | 7/1997 | Rhee et al. |
| 5,656,035 A | 8/1997 | Avoy |
| 5,672,622 A | 9/1997 | Hedgepeth et al. |
| 5,681,576 A | 10/1997 | Henry |
| 5,702,361 A | 12/1997 | Evans et al. |
| 5,741,223 A | 4/1998 | Janzen et al. |
| 5,744,545 A | 4/1998 | Rhee et al. |

(Continued)

FOREIGN PATENT DOCUMENTS

EP 0732109 A1 9/1996

(Continued)

OTHER PUBLICATIONS

International Search Report from Application No. EP 08 25 0526 mailed Jan. 7, 2009.

(Continued)

*Primary Examiner* — Robert A Wax
*Assistant Examiner* — Danah Al-Awadi

(57) ABSTRACT

Drug delivery devices are provided herein including crosslinked polymeric compositions. The devices may, in embodiments, possess at least two drug release profiles, in embodiments at least three drug release profiles.

23 Claims, No Drawings

U.S. PATENT DOCUMENTS

| | | | |
|---|---|---|---|
| 5,749,968 | A | 5/1998 | Melanson et al. |
| 5,752,974 | A | 5/1998 | Rhee et al. |
| 5,773,025 | A | 6/1998 | Baichwal |
| 5,786,421 | A | 7/1998 | Rhee et al. |
| 5,800,541 | A | 9/1998 | Rhee et al. |
| 5,801,033 | A | 9/1998 | Hubbell et al. |
| 5,807,581 | A | 9/1998 | Rosenblatt et al. |
| 5,810,885 | A | 9/1998 | Zinger |
| 5,844,023 | A | 12/1998 | Tomka |
| 5,858,746 | A | 1/1999 | Hubbell et al. |
| 5,863,551 | A | 1/1999 | Woerly |
| 5,874,500 | A | 2/1999 | Rhee et al. |
| 5,932,462 | A | 8/1999 | Harris et al. |
| 5,936,035 | A | 8/1999 | Rhee et al. |
| 5,962,023 | A | 10/1999 | Jamiolkowski et al. |
| 5,986,043 | A | 11/1999 | Hubbell et al. |
| 6,017,301 | A | 1/2000 | Schwartz et al. |
| 6,033,654 | A | 3/2000 | Stedronsky et al. |
| 6,051,248 | A | 4/2000 | Sawhney et al. |
| 6,051,648 | A | 4/2000 | Rhee et al. |
| 6,110,484 | A | 8/2000 | Sierra |
| 6,124,273 | A | 9/2000 | Drohan et al. |
| 6,149,931 | A | 11/2000 | Schwartz et al. |
| 6,153,211 | A | 11/2000 | Hubbell et al. |
| 6,156,531 | A | 12/2000 | Pathak et al. |
| 6,162,241 | A | 12/2000 | Coury et al. |
| 6,165,489 | A | 12/2000 | Berg et al. |
| 6,166,130 | A | 12/2000 | Rhee et al. |
| 6,201,065 | B1 | 3/2001 | Pathak et al. |
| 6,214,966 | B1 | 4/2001 | Harris |
| 6,258,351 | B1 | 7/2001 | Harris |
| 6,271,278 | B1 | 8/2001 | Park et al. |
| 6,277,394 | B1 | 8/2001 | Sierra |
| 6,306,922 | B1 | 10/2001 | Hubbell et al. |
| 6,312,725 | B1 | 11/2001 | Wallace et al. |
| 6,323,278 | B2 | 11/2001 | Rhee et al. |
| 6,428,571 | B1 | 8/2002 | Lentz et al. |
| 6,458,147 | B1 | 10/2002 | Cruise et al. |
| 6,458,889 | B1 | 10/2002 | Trollsas et al. |
| 6,465,001 | B1 | 10/2002 | Hubbell et al. |
| 6,566,406 | B1 * | 5/2003 | Pathak et al. ............ 514/772.1 |
| 6,818,018 | B1 | 11/2004 | Sawhney |
| 7,009,034 | B2 | 3/2006 | Pathak et al. |
| 7,160,557 | B2 * | 1/2007 | Bernstein et al. ............ 424/486 |
| 7,312,301 | B2 * | 12/2007 | Fang et al. ............ 528/391 |
| 2001/0003126 | A1 | 6/2001 | Rhee et al. |
| 2003/0012734 | A1 | 1/2003 | Pathak |
| 2004/0076602 | A1 | 4/2004 | Harris et al. |

FOREIGN PATENT DOCUMENTS

| | | |
|---|---|---|
| EP | 1 704 878 | 9/2006 |
| EP | 1967220 | 9/2008 |
| WO | WO 91/09641 A1 | 7/1991 |
| WO | WO 96/03159 A1 | 2/1996 |
| WO | WO 96/14095 A1 | 5/1996 |
| WO | WO 97/22371 A1 | 6/1997 |
| WO | WO 97/22372 A1 | 6/1997 |
| WO | WO 98/35631 A1 | 8/1998 |
| WO | WO 99/10022 | 3/1999 |
| WO | WO 99/14259 | 3/1999 |
| WO | WO 99/22770 A1 | 5/1999 |
| WO | WO 99/34833 C2 | 7/1999 |
| WO | WO 01/66017 | 9/2001 |

OTHER PUBLICATIONS

European Search Report for EP 08252635.1-2112 date of completion is Jan. 7, 2009 (3 pages).

US 6,214,374, 04/2001, Schmirler et al. (withdrawn)

* cited by examiner

DRUG DELIVERY DEVICE

CROSS-REFERENCE TO RELATED APPLICATIONS

This application claims the benefit of and priority to U.S. Provisional Patent Application No. 60/964,488, filed Aug. 13, 2007, the entire disclosure of which is incorporated by reference herein.

TECHNICAL FIELD

The present disclosure relates generally to biocompatible crosslinked polymers, methods for preparing and using same, and the use of these polymers to release drugs in vivo.

BACKGROUND

Biocompatible crosslinked polymers may be used in drug and surgical treatments of various disease states found in animals, including humans. Biocompatible crosslinked polymers may be formed by various methods. For example, U.S. Pat. No. 5,410,016 discloses the use of free radical photopolymerizable monomers to form biocompatible crosslinked polymers. Other biocompatible crosslinked polymers used for medical applications include polymers formed using electrophilic-nucleophilic polymerization, including those disclosed in U.S. Pat. Nos. 5,296,518, 5,104,909, 5,514,379, 5,874,500, and 5,527,856.

The systemic administration of drugs is known. Suitable routes of administration include, for example, oral, parenteral, buccal, peroral, nasal, rectal, intravenous, intramuscular, subcutaneous, intracisternal, intravaginal, intraperitonal, intravesical, intraventricular, intracranial, intrathecal, topical and/or transdermal, combinations thereof, and the like. In some cases, administration may require a high systemic concentration, which may be accompanied by adverse side effects. Similarly, the use of extended release forms of medicaments, while desirable to prolong the time period during which the effects of a particular drug may be observed, may require the use of mechanisms or systems that are inefficient in the release of the medicament in a desired amount.

There remains a need for improved biocompatible crosslinked polymers and their use as drug delivery devices.

SUMMARY

The present disclosure provides compositions suitable for use as drug delivery devices. In embodiments, a drug delivery device of the present disclosure may include a biocompatible crosslinked polymer hydrogel, and at least one drug. The biocompatible crosslinked polymer hydrogel may have at least three drug release profiles including a first drug release profile of from about 0 days to about 10 days, a second drug release profile of from about 0 days to about 30 days, and a third release profile of from about 0 days to about 180 days.

In embodiments, suitable hydrogels utilized in the drug delivery devices of the present disclosure may include at least one biocompatible crosslinker region including a crosslinked synthetic crosslinker molecule with a pre-crosslinked molecular weight of less than about 2000, and at least one biocompatible functional polymer region including a crosslinked synthetic polymer molecule with a pre-crosslinked molecular weight of more than about 7 times the molecular weight of the pre-crosslinked crosslinker molecule. The biocompatible crosslinked polymer may possess links, in embodiments at least three links, between the crosslinker region and the functional polymer region, which links may be the reaction product of at least one electrophilic functional group with at least one nucleophilic functional group.

Drug delivery devices of the present disclosure may be utilized to release a single drug at varying times, different drugs at varying times, or combinations of the same or different drugs at varying times.

DETAILED DESCRIPTION

The drug delivery devices of the present disclosure may have differing release profiles for the same, or different, bioactive agents. In embodiments, the drug delivery devices may be formed from biocompatible crosslinked polymers formed from the reaction of precursors having electrophilic and nucleophilic functional groups. The precursors may be water soluble, non-toxic and biologically acceptable. Suitable polymers for forming such compositions include, for example, those disclosed in U.S. Pat. No. 6,566,406, the entire disclosure of which is incorporated by reference herein.

In embodiments, at least one of the precursors may be a small molecule, and may be referred to herein, in embodiments, as a "crosslinker". Suitable crosslinkers may, prior to reacting with other precursors to form a composition of the present disclosure, have a solubility of at least about 1 g/100 mL in an aqueous solution, in embodiments water. Crosslinkers may have a molecular weight of less than about 2000, in embodiments from about 100 to about 2000, in other embodiments from about 450 to about 650. One of the other precursors utilized to form a composition of the present disclosure may be a macromolecule, and may be referred to herein, in embodiments, as a "functional polymer". In embodiments, the functional polymer may include a synthetic polymer molecule, in embodiments a water soluble synthetic polymer, having a pre-crosslinked molecular weight of more than about 7 times the molecular weight of the crosslinker, in embodiments from about 7 times to about 50 times greater than the molecular weight of the crosslinker, in other embodiments from about 12 times to about 35 times greater than the molecular weight of the crosslinker.

In some embodiments, each precursor may be multifunctional, meaning that they may include two or more electrophilic or nucleophilic functional groups, such that a nucleophilic functional group on one precursor may react with an electrophilic functional group on another precursor to form a covalent bond. At least one of the precursors may possess more than two functional groups, so that the precursors may combine to form crosslinked polymeric products as a result of the electrophilic-nucleophilic reaction. In embodiments, such reactions may be referred to as "crosslinking reactions".

In embodiments, each precursor may possess only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines. Thus, functional polymers such as proteins, poly(allyl amines), or amine-terminated di- or multifunctional poly(ethylene glycols) ("PEG") can be used in some embodiments.

In other embodiments, the precursors may possess biologically inert and water soluble cores. When the core is a polymeric region that is water soluble, suitable polymers that may be used include, but are not limited to, polyethers, for example polyalkylene oxides such as polyethylene glycol ("PEG"), polyethylene oxide ("PEO"), polyethylene oxide-co-polypropylene oxide ("PPO"), co-polyethylene oxide block or random copolymers; polyvinyl alcohol ("PVA"); poly(vinyl pyrrolidinone) ("PVP"); poly(amino acids); dextran; combinations of the foregoing, and the like. Polyethers such as poly(oxyalkylenes) or poly(ethylene oxide) may be useful in some embodiments. When the core is small, any of a variety of hydrophilic functionalities can be used to make the precursor water soluble. For example, functional groups like hydroxyl, amine, sulfonate and carboxylate, may be used to make the precursor water soluble. In addition, the N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

The crosslinking reactions may occur in aqueous solution under physiological conditions. In embodiments, the crosslinking reactions occur "in situ", meaning they occur at local sites such as on organs or tissues in a living animal or human body. In some embodiments, the crosslinking reactions do not release heat during polymerization. The crosslinking reaction leading to gelation may occur within about 10 minutes, in embodiments within about 2 minutes, in other embodiments within about one minute, in yet other embodiments within about 30 seconds, in other embodiments within about 4 seconds. Gel time may be determined by a gel time measurement obtained by methods within the purview of those skilled in the art.

Certain functional groups, such as alcohols or carboxylic acids, do not normally react with other functional groups, such as amines, under physiological conditions (e.g., pH from about 7.2 to about 11, at a temperature of about 37° C.). However, such functional groups can be made more reactive by using an activating group such as N-hydroxysuccinimide. Methods for activating such functional groups are within the purview of those skilled in the art. Suitable activating groups include, but are not limited to, carbonyldiimidazole, sulfonyl chloride, aryl halides, sulfosuccinimidyl esters, N-hydroxysuccinimidyl esters, succinimidyl esters, epoxides, aldehydes, maleimides, imidoesters and the like. The N-hydroxysuccinimide esters or N-hydroxysulfosuccinimide groups may be utilized, in embodiments, for crosslinking of proteins or amine functionalized polymers such as amino terminated polyethylene glycol ("APEG").

In embodiments, suitable polymers include functional polymers such as linear water soluble and biodegradable functional polymers, which may be end-capped with two functional groups (e.g., N-hydroxysuccinimide ester (NHS), epoxide or similar reactive groups). The water soluble core may be a polyalkylene oxide, such as a polyethylene glycol block copolymer, which may be extended with at least one biodegradable linkage between it and each terminal functional group. The biodegradable linkage may be a single linkage or copolymers or homopolymers of absorbable polymers and copolymers of poly(hydroxy acid)s, poly(orthocarbonate)s, poly(anhydride)s, poly(lactone)s, poly(aminoacid)s, poly(carbonate)s, poly(phosphonate)s, combinations thereof, and the like.

Other suitable water-soluble linear polymers include polyethylene glycols terminated with reactive end group such as primary amines and/or thiols. Such polymers include those commercially available from Sigma (Milwaukee, Wis.) and Shearwater Polymers (Huntsville, Ala.). Some other suitable difunctional polymers are PPO-PEO-PPO block copolymers such as PLURONIC F68 terminated with amine groups. PLURONIC or TETRONIC polymers are available with terminal hydroxyl groups. The hydroxyl groups may be converted into amine groups utilizing methods within the purview of those skilled in the art.

Other functional polymers may be branched or star shaped biodegradable functional polymers which have an inert, water soluble polymer at the center. The inert and water soluble core may be terminated with oligomeric biodegradable extensions which, in turn, may be terminated with reactive functional groups.

Some suitable polymers may include multifunctional 4 arm biodegradable functional polymers. These polymers may have a water-soluble core at the center, such as a 4 arm, tetrafunctional polyethylene glycol or a block copolymer of PEO-PPO-PEO, which may be extended with small oligomeric extensions of biodegradable polymers to maintain water solubility and terminated with reactive functional end-groups such as Carbodiimide (CDI) or NHS. Other multifunctional polymers with multiple arms may be utilized having 6 arms, 8 arms, 10 arms, 12 arms, and the like.

Other suitable functional polymers include multifunctional star or graft type biodegradable polymers such as polyethylene oxide, polyvinyl alcohol, or poly(vinyl pyrrolidinone) at the core, which may be completely or partially extended with biodegradable polymers. The biodegradable polymers may, in embodiments, be terminated with reactive end groups.

Small molecule crosslinkers may also be used, where the core includes a small molecule like ethoxylated glycerol, inositol, trimethylolpropane, and the like to form the resulting crosslinker. In addition, biodegradable extensions may include small molecules like succinate or glutarate or combinations of 2 or more esters, such as glycolate/2-hydroxybutyrate or glycolate/4-hydroxyproline, and the like. A dimer or trimer of 4-hydroxyproline may be used to not only add degradability, but also to add nucleophilic reactive sites via the pendant primary amines which are part of the hydroxyproline moiety.

Other variations of the core, the biodegradable linkages, and the terminal functional groups may be constructed so long as the resulting functional polymer has the properties of low tissue toxicity, water solubility, and reactivity with other functional groups, i.e., in embodiments electrophilic groups on the functional polymer which may react with nucleophilic functional groups on the crosslinker, or nucleophilic groups on the functional polymer which may react with electrophilic functional groups on the crosslinker.

Cores may also be terminated with a reactive functional group that is also water solubilizing, such a N-hydroxysulfosuccinimide ester ("SNHS") or N-hydroxyethoxylated succinimide ester ("ENHS"). For example, suitable oligomers and polymers may be made of a poly(hydroxy acid) such as poly(lactic acid), which is insoluble in water. However, the terminal carboxylic acid group of these oligomers or polymers can be activated with N-hydroxysulfosuccinimide ester ("SNHS") or N-hydroxyethoxylated succinimide ester ("ENHS") groups. An ionic group, like a metal salt (for example, sodium salt) of sulfonic acid, or a nonionic group, like a polyethylene oxide on the succinimide ring, may provide water solubility while the NHS ester provides chemical reactivity towards amines. The sulfonate groups (sodium salts) or ethoxylated groups on the succinimide ring may solubilize the oligomer or polymer without appreciably inhibiting reactivity towards amine groups.

Other precursors which may be utilized in forming the drug delivery devices herein include multifunctional graft or branch type water-soluble copolymers with terminal amine groups. For example, small molecule crosslinkers may be utilized including a small molecule like ethoxylated glycerol, ethoxylated pentaerythritol, inositol, trimethylolpropane, dilysine, trilysine, tetralysine, and the like, to form the resulting crosslinker.

If it is desired that the biocompatible crosslinked polymer be biodegradable or absorbable, one or more precursors having biodegradable linkages may be used. The biodegradable linkage may be between the functional groups and may optionally also serve as the water soluble core of one or more of the precursors. In the alternative, or in addition, the functional groups of the precursors may be chosen such that the product of the reaction between them results in a biodegradable linkage. For each approach, biodegradable linkages may be chosen such that the resulting biodegradable biocompatible crosslinked polymer may degrade under physiological conditions into non-toxic products or be absorbed over a desired period of time.

The biodegradable linkage may be chemically or enzymatically hydrolyzable or absorbable. Illustrative chemically hydrolyzable biodegradable linkages include polymers, copolymers and oligomers of glycolide, dl-lactide, l-lactide, caprolactone, dioxanone, trimethylene carbonate, combinations thereof, and the like. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(aminoacid)s, poly(carbonate)s, poly(phosphonate)s, combinations thereof, and the like.

In yet other embodiments, suitable biodegradable linkages that are hydrolytically degradable which may be utilized in the compositions of the present disclosure include, but are not limited to, esters, anhydrides, phosphoesters, combinations thereof, and the like. Other suitable biodegradable linkages which may be enzymatically degradable and included in the compositions of the present disclosure include, but are not limited to: an amino acid residue such as -Arg-, -Ala-, -Ala (D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, combinations of any of the foregoing, and the like. Those skilled in the art will readily envision reaction schemes for incorporating enzymatically degradable linkages into the crosslinked polymers of the present disclosure.

Methods for forming these polymers and their precursors are within the purview of those skilled in the art and include, for example, those disclosed in U.S. Pat. No. 6,566,406, the entire disclosure of which is incorporated by reference herein.

In embodiments, suitable reactive groups which may be utilized to form the compositions of the present disclosure include N-hydroxysuccinimide esters, which may be synthesized by any of several methods. For example, hydroxyl groups may be converted to carboxylic groups by reacting them with anhydrides such as succinic anhydride in the presence of tertiary amines such as pyridine or triethylamine or dimethylaminopyridine ("DMAP"). Other anhydrides such as glutaric anhydride, phthalic anhydride, maleic anhydride and the like may also be used. The resulting terminal carboxyl groups may then be reacted with N-hydroxysuccinimide in the presence of dicyclohexylcarbodiimide ("DCC") to produce an N-hydroxysuccinimide ester (referred to, in embodiments, as NHS activation).

The synthetic crosslinked gels described above may degrade due to hydrolysis of the biodegradable region. The degradation of gels containing synthetic peptide sequences may depend on the action of a specific enzyme and its concentration. In some cases, a specific enzyme may be added during the crosslinking reaction to accelerate the degradation process. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the crosslinked polymer of the present disclosure. Methods for incorporating enzymes into liposomes and/or microspheres are within the purview of those skilled in the art.

When the crosslinker and functional polymers are synthetic (for example, when they are based on polyalkylene oxide), it may be desirable to use molar equivalent quantities of the reactants. In some cases, excess molar crosslinker may be added to compensate for side reactions, such as reactions due to hydrolysis of the functional group.

When choosing the crosslinker and crosslinkable polymer, at least one of the polymers may have more than 2 functional groups per molecule and at least one degradable region, if it is desired that the resulting biocompatible crosslinked polymer be biodegradable. Generally, each biocompatible crosslinked polymer precursor may have more than 2 and, in some embodiments, more than 4 functional groups.

As noted above, in embodiments the polymer compositions suitable for forming the drug delivery devices herein may be formed from the reaction of electrophilic groups on one precursor with nucleophilic groups on a second precursor. Suitable electrophilic groups include NHS, SNHS and ENHS. Suitable nucleophilic groups include primary amines. The NHS-amine reaction may possess reaction kinetics which leads to quick gelation, usually within 10 minutes, in embodiments within 1 minute, in other embodiments within 10 seconds. This fast gelation may be desirable for in situ reactions on live tissue.

The NHS-amine crosslinking reaction leads to formation of N-hydroxysuccinimide as a side product. The sulfonated or ethoxylated forms of N-hydroxysuccinimide may be useful due to their increased solubility in water and hence their rapid clearance from the body. The sulfonic acid salt on the succinimide ring does not alter the reactivity of the NHS group with the primary amines.

The NHS-amine crosslinking reaction may be carried out in aqueous solutions and in the presence of buffers. Suitable buffers include phosphate buffer (pH from about 5 to about 7.5), triethanolamine buffer (pH from about 7.5 to about 9), borate buffer (pH from about 9 to about 12), and sodium bicarbonate buffer (pH from about 9 to about 10).

Aqueous solutions of NHS based crosslinkers and functional polymers may be made just before the crosslinking reaction due to reaction of NHS groups with water. Longer "pot life" may be obtained by keeping these solutions at a lower pH (for example, a pH from about 4 to about 5).

The crosslinking density of the resulting biocompatible crosslinked polymer may be controlled by the overall molecular weight of the crosslinker and functional polymer and the number of functional groups available per molecule. A lower molecular weight between crosslinks, such as 600 Da, may result in higher crosslinking density as compared to a higher molecular weight, such as 10,000 Da. Higher molecular weight functional polymers may be useful, in embodiments having a molecular weight of more than about 3000 Da, so as to obtain elastic gels.

The crosslinking density may also be controlled by the overall percent solids of the crosslinker and functional polymer solutions. Increasing the number of reactive groups increases the number of degradable crosslinks in the resulting hydrogel. Increasing the percent solids may also increase the probability that an electrophilic group will combine with a nucleophilic group prior to inactivation by hydrolysis. Yet another method to control crosslink density is by adjusting the stoichiometry of nucleophilic groups to electrophilic groups. A one to one ratio may result in a higher crosslink density.

Where proteins are utilized to form the polymer, the resulting crosslinked hydrogel may be a semisynthetic hydrogel whose degradation depends on the degradable segment in the crosslinker as well as degradation of the protein, for example albumin, by enzymes. In the absence of any degradable enzymes, the crosslinked polymer may degrade solely by the hydrolysis of the biodegradable segment. If polyglycolate is used as the biodegradable segment, the crosslinked polymer may degrade over a period of time of from about 1 day to about 30 days, depending on the crosslinking density of the network. Similarly, a polycaprolactone based crosslinked network may degrade over a period of time of from about 1 month to about 8 months. The degradation time may vary according to the type of degradable segment used, in the following order:

polyglycolate<polylactate<polytrimethylene carbonate<polycaprolactone.

Thus, it is possible to construct a hydrogel with a desired degradation profile, from a few days to months, using a proper degradable segment. The degradation rate may also vary by the anhydride chosen to create the degradable linkage for a single ester, in the following order:

succinate<glutarate<methyl glutarate.

The hydrophobicity generated by biodegradable blocks such as oligohydroxy acid blocks or the hydrophobicity of PPO blocks in PLURONIC or TETRONIC polymers may be helpful in dissolving small organic drug molecules. Other properties which may be affected by incorporation of biodegradable or hydrophobic blocks include: water absorption, mechanical properties and thermosensitivity.

In embodiments, the resulting crosslinked polymer may include at least one ester linkage between the crosslinker regions and the functional polymer regions, in embodiments from about 1 ester link to about 20 ester links between the crosslinker regions and the functional polymer regions, in other embodiments from about 3 ester links to about 12 ester links between the crosslinker regions and the functional polymer regions. As noted above, in embodiments the links may be the reaction product of at least one electrophilic group with at least one nucleophilic group. In embodiments these links may be biodegradable and/or enzymatically degradable.

In accordance with the present disclosure, the crosslinked polymers may be utilized as drug delivery devices. As used herein, the terms "drug", "bioactive agent", and "biologically active agent", are used interchangeably. Depending upon the polymers and crosslinkers utilized in forming the compositions herein, a drug may be merely incorporated into the polymeric matrix, without binding to the matrix. Alternatively, or in addition, a drug may be covalently bound to the polymeric matrix through a pendant linkage or incorporated into the polymer backbone during the crosslinking reaction, either separately or as part of either precursor. Utilizing multiple means for attachment or incorporation of a drug into a crosslinked polymer of the present disclosure may allow for one to form a drug delivery device possessing multiple release profiles. For example, a drug merely incorporated into a polymeric matrix, which is not covalently bound thereto, may be released from said matrix more rapidly than a drug covalently bound to the same matrix. Similarly, a drug attached to the polymeric matrix through a pendant linkage, i.e., which projects from the backbone of the crosslinked polymer, may be released more rapidly than a drug that is incorporated into the backbone of the crosslinked polymer.

In embodiments, the drug release profile of a drug from the crosslinked polymeric compositions of the present disclosure may thus be determined by different mechanisms, including the water solubility of the drug, the hydrolysis of the hydrogel, and the mass loss of the hydrogel.

In accordance with the present disclosure, the crosslinked polymer may be utilized to release the same, or a different drug, at different points in time after formation of the crosslinked polymer in situ. For example, in some embodiments, a first drug may be both incorporated into the matrix formed by the crosslinked polymer, with additional drug covalently bound to the crosslinked polymer. As noted above, in some embodiments the drug covalently bound to the crosslinked polymer may be bound by pendant linkages, incorporated into the backbone of the crosslinked polymer, or both. Thus, for the same drug, there may exist at least two different release profiles of the drug from the crosslinked polymer: an initial release of drug that is not bound by, but merely incorporated within, the polymeric matrix formed by the crosslinked polymer of the present disclosure (which, in embodiments will be dependent on the water solubility of the drug); and a second release of drug that is covalently bound to the crosslinked polymer (which, in embodiments will be dependent on the hydrolysis of the hydrogel and/or the mass loss of the hydrogel). As noted above, covalent linkage of a drug to the crosslinked polymer may be by pendant linkages or by incorporation into the backbone of the polymer.

In embodiments, drugs attached by pendant linkages may have multiple release profiles. A drug attached through a degradable linkage, for example an ester on the crosslinked polymer (which, in embodiments, would link an amine on the drug) would be released when the ester hydrolyzed. A drug attached through a non-degradable linkage, for example an amine on the crosslinked polymer (which, in embodiments, would link an ester such as NHS on the drug), would be released through mass loss of the crosslinked polymer of the present disclosure.

In other embodiments, there may exist at least three different release profiles of the drug from the crosslinked polymer: an initial release of drug that is not bound, but merely incorporated within, the polymeric matrix formed by the crosslinked polymer of the present disclosure; a second release of drug that is covalently bound to the crosslinked polymer through degradable pendant linkages; and a third release of drug that is covalently bound to the crosslinked polymer by being incorporated into the backbone of the polymer or is covalently bound to the crosslinked polymer through non-degradable pendant linkages. In embodiments, the first release profile may depend upon the water solubility of the drug, the second release profile may depend upon the hydrolysis of the hydrogel, and the third release profile may depend upon the mass loss of the hydrogel.

In yet other embodiments, instead of only a single drug being released from the crosslinked polymer at different times, multiple drugs may be released from the crosslinked polymer of the present disclosure at different times. Thus, a first drug merely incorporated into the polymeric matrix but not bound thereto may be released either immediately or shortly after formation of the crosslinked polymer in situ, while a second drug covalently bound to the crosslinked polymer through pendant linkages or incorporated into the polymer backbone may be released later. Similarly, where three drugs are included in the crosslinked polymer of the present disclosure, a first drug incorporated into the polymeric matrix but not bound thereto may be released either immediately or shortly after formation of the crosslinked polymer in situ; a second drug covalently bound to the crosslinked polymer through a degradable linkage such as a pendant ester linkage may be released later by hydrolysis; and a third drug covalently bound to the crosslinked polymer by a pendant nondegradable linkage (such as an amine linkage) or incorporated into the polymeric backbone may be released last.

As noted above, combinations of drugs may be released from compositions of the present disclosure at varying times. For example, more than one drug may be released during a first release profile, a second release profile, a third release profile, and the like.

Examples of suitable drugs which may be delivered by a crosslinked polymer of the present disclosure include, but are not limited to, antimicrobial agents, protein and peptide preparations, antipyretic, antiphlogistic and analgesic agents, anti-inflammatory agents, vasodilators, antihypertensive and antiarrhythmic agents, hypotensive agents, antitussive agents, antineoplastic agents, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, glycosaminoglycans, carbohydrates, nucleic acids, inorganic and organic biologically active compounds, combinations thereof, and the like. Specific biologically active agents include, but are not limited to, enzymes, angiogenic agents, anti-angiogenic agents, growth factors, antibodies, neurotransmitters, psychoactive drugs, anticancer drugs, antimicrobial agents including antibiotics such as rifampin, chemotherapeutic drugs, drugs affecting reproductive organs, genes, oligonucleotides, combinations thereof, and the like.

In embodiments, these bioactive agents may also possess functional groups capable of reacting with the crosslinker, the functional polymer, or both. When these biologically active agents also contain functional groups, the functional groups of the bioactive agent can react with the components of the crosslinked polymer compositions of the present disclosure, thereby becoming either attached thereto through a pendant linkage or incorporated in the backbone of the resulting crosslinked polymer.

As noted above, in embodiments a first drug may have one release profile, with a second and/or optional third drug having a different release profile. Nonlimiting examples of drugs which may be administered utilizing the crosslinked polymer compositions of the present disclosure and the varying release profiles which may be desirable for such drugs, in embodiments, are summarized below in Table 1.

TABLE 1

| 0-3 days | 0-30 days | 0-90 days |
|---|---|---|
| Hemostatic agents | Analgesics | Anti-cancer agents |
| Topical anesthetics | anti-inflammatories | anti-scarring agents |
| Anti-adhesion agents | Anti-adhesion agents | proteins: BMP's, VGF, TGF-beta |
| Antibiotics | antibiotics | |

Thus, in embodiments, the time of release of a first agent may be from about 0 days to about 10 days, the time of release of a second agent may be from about 0 days to about 30 days, and the time of release of a third agent may be from about 0 days to about 180 days. In other embodiments, the time of release of a first agent may be form about 2 days to about 8 days, the release of a second agent may be from about 9 days to about 29 days and the release of a third drug may be from about 30 days to about 120 days.

Various combinations of the above drugs and different release profiles may be utilized. Thus, depending upon the condition to be treated, one could select the desired drug, determine the desired release rate of such drug, and then incorporate the drug in a crosslinked polymer of the present disclosure as described above through physical or chemical incorporation, thereby achieving the desired rate of release from the crosslinked polymer of the present disclosure. For example, for wound healing, it may be desirable to have a drug delivery device including a crosslinked polymer of the present disclosure initially release a hemostatic agent, anti-adhesion agent, or combinations thereof, followed by the release of an anti-inflammatory agent, followed by the release of an anti-scarring agent. For cardiac surgery, it may be desirable for a drug delivery device including a crosslinked polymer of the present disclosure to initially release an anti-adhesion agent, followed by a long-term release of an anti-arrhythmic agent.

Moreover, the crosslinked polymer itself, in embodiments, possesses anti-adhesion properties which may be utilized in conjunction with additional drugs as described above. Thus, in embodiments, the crosslinked polymer itself may be used as an anti-adhesion agent, an adhesive, or a sealant, with additional drugs incorporated therein or bound thereto for other indications.

In embodiments, imaging agents such as iodine or barium sulfate, or fluorine, can also be combined with the compositions of the present disclosure to allow visualization of the polymer at the time of application or thereafter through the use of imaging equipment, including X-ray, MRI, and CAT scan equipment. Other imaging agents which may be included are within the purview of those skilled in the art and include, but are not limited to, substances suitable for use in medical implantable medical devices, such as FD&C dyes 3 and 6, eosin, methylene blue, indocyanine green, or colored dyes normally found in synthetic surgical sutures. Suitable colors include green and/or blue because such colors may have better visibility in the presence of blood or on a pink or white tissue background.

The imaging agents may be added in small amounts, in embodiments less than about 1% weight/volume, in other embodiments less than about 0.01% weight/volume, and in yet other embodiments less than about 0.001% weight/volume concentration.

In embodiments, the drug delivery devices including the above biocompatible crosslinked polymers may be formed "in situ" at a surgical site in the body. In other embodiments, the components and drugs may be combined prior to application, thus pendant attachment of a drug or incorporation of a drug into the backbone of a precursor may first occur ex vivo, with the rest of drug incorporation and polymer formation occurring in situ.

In using the crosslinked composition for drug delivery as mentioned above, the amount of functional polymer, crosslinker and the bioactive agent introduced in the host may depend upon the particular drug and the condition to be treated. Administration may be by any convenient means such as syringe, cannula, trocar, catheter and the like. Methodologies and devices for performing "in situ" gelation, developed for other adhesive or sealant systems such as fibrin glue or sealant applications, may be used herein. In embodiments, one may use specialized devices to apply the precursor solutions, such as those described in U.S. Pat. Nos. 4,874,368, 4,631,055, 4,735,616, 4,359,049, 4,978,336, 5,116,315, 4,902,281, 4,932,942, and International Application No. WO 91/09641, the entire disclosures of each of which are incorporated by reference herein.

To prepare drug delivery devices herein, the bioactive agents described above may be mixed with the crosslinkable polymer precursors prior to crosslinking the polymer or during the aseptic manufacturing of the functional polymer, the crosslinker, or both. In embodiments, functional polymers made from inert polymers like PLURONIC, TETRONICS or TWEEN components may be suitable in releasing small molecule hydrophobic drugs. As described above, the bioactive agent may be merely physically incorporated in the resulting polymeric matrix, covalently bound thereto, or both.

In embodiments, the active agent or agents may also be present in a separate phase when a crosslinker and crosslinkable functional polymers are reacted to produce a crosslinked polymer network or gel. This phase separation may prevent participation of the bioactive substance in the chemical crosslinking reaction such as the reaction between NHS esters and amine groups, which may be desirable in some embodiments. The separate phase may also help to modulate the release kinetics of the active agent from the crosslinked material or gel, where the "separate phase" could be an oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride)s, poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glues or fibrin sealants, caging and entrapping molecules, like cyclodextrin, molecular sieves, and the like. Microspheres made from polymers and copolymers of poly(lactone)s and poly(hydroxy acid)s may be useful as biodegradable encapsulation vehicles.

In embodiments, the functional polymer along with bioactive agent, with or without an encapsulating vehicle, may be administered to the host along with an equivalent amount of crosslinker and aqueous buffers. The chemical reaction between crosslinker and the functional polymer solution readily takes place to form a crosslinked gel and acts as a depot for release of the active agent to the patient. As noted above, in other embodiments the bioactive agent may become linked to the polymer through a pendant linkage or, in other embodiments, incorporated into the polymer backbone during crosslinking. Such methods of drug delivery may be useful in both systemic and local administration of an active agent.

Controlled rates of drug delivery also may be obtained with the system of the present disclosure by the degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

It will be appreciated that various of the above-disclosed and other features and functions, or alternatives thereof, may be desirably combined with many other systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A drug delivery device, comprising:
   a biocompatible crosslinked polymer hydrogel comprising a backbone; and
   at least one drug,
   wherein the biocompatible crosslinked polymer hydrogel comprises at least three drug release profiles comprising a first drug release profile of from about 0 days to about 10 days, a second drug release profile of from about 0 days to about 30 days, and a third drug release profile of from about 0 days to about 180 days, and wherein the at least one drug having the first drug release profile is incorporated into the crosslinked polymer hydrogel without binding, the at least one drug having said second drug release profile is incorporated into the crosslinked polymer hydrogel by a means selected from the group consisting of bound by a pendant linkage and incorporated into the backbone, and the at least one drug having said third drug release profile is incorporated into the crosslinked polymer hydrogel by a means selected from the group consisting of bound by a pendant linkage and incorporated into the backbone.

2. The drug delivery device of claim 1, wherein the hydrogel comprises:
   at least one biocompatible crosslinker region comprising a crosslinked synthetic crosslinker molecule with a pre-crosslinked molecular weight of less than about 2000; and
   at least one biocompatible functional polymer region comprising a crosslinked synthetic polymer molecule with a pre-crosslinked molecular weight of more than about 7 times the molecular weight of the pre-crosslinked crosslinker molecule,
   wherein the biocompatible crosslinked polymer comprises at least three links between the crosslinker region and the functional polymer region, and the links are a reaction product of at least one electrophilic functional group with of at least one nucleophilic functional group that react to form the hydrogel.

3. The drug delivery device of claim 2, wherein the biocompatible crosslinker region of the hydrogel has a solubility of at least 1 g/100 ml in an aqueous solution.

4. The drug delivery device of claim 2, wherein the biocompatible crosslinked polymer further comprises at least one biodegradable link.

5. The drug delivery device of claim 2, wherein at least one of the links between the crosslinker and functional polymer region of the hydrogel is biodegradable.

6. The drug delivery device of claim 1, wherein the hydrogel comprises a crosslinked biocompatible material comprising:
   a crosslinker having a water solubility of at least about 1 gram per 100 milliliters and a molecular weight of from about 100 to about 2000; and
   a water soluble synthetic polymer joined to the crosslinker by covalent bonds, the synthetic polymer possessing a molecular weight of at least about 7 times the molecular weight of the crosslinker,
   wherein the covalent bonds are a reaction product of at least one electrophile and at least one nucleophile.

7. The drug delivery device of claim 6, wherein the electrophiles and nucleophiles cause the biocompatible material to have a gel time of less than about 2 minutes as measured by a gel time measurement.

8. The drug delivery device of claim 6, wherein the electrophiles and nucleophiles cause the biocompatible material to have a gel time of less than about 4 seconds.

9. The drug delivery device of claim 6, wherein the synthetic polymer molecular weight is from about 12 times to about 35 times greater than the molecular weight of the crosslinker.

10. The drug delivery device of claim 6, wherein the at least one crosslinker is selected from the group consisting of dilysine, trilysine, and tetralysine.

11. The drug delivery device of claim 1, wherein the at least one drug is selected from the group consisting of antimicrobial agents, proteins, peptides, antipyretic agents, antiphlogistic agents, analgesic agents, anti-inflammatory agents, vasodilators, antihypertensive agents, antiarrhythmic agents, hypotensive agents, antitussive agents, antineoplastic agents, local anesthetics, hormone preparations, antiasthmatic agents, antiallergic agents, antihistaminics, anticoagulants, antispasmodics, cerebral circulation improvers, metabolism improvers, antidepressants, antianxiety agents, vitamin D preparations, hypoglycemic agents, antiulcer agents, hypnotics, antibiotics, antifungal agents, sedative agents, bronchodilator agents, antiviral agents, dysuric agents, glycosaminoglycans, carbohydrates, nucleic acids, inorganic biologically active compounds, organic biologically active compounds, enzymes, angiogenic agents, anti-angiogenic agents, growth factors, antibodies, neurotransmitters, psychoactive drugs, anticancer drugs, chemotherapeutic drugs, drugs affecting reproductive organs, genes, oligonucleotides, and combinations thereof.

12. The drug delivery device of claim 1, wherein the at least one drug released from the hydrogel during the three drug release profiles is the same drug.

13. The drug delivery device of claim 1, wherein the at least one drug released from the hydrogel during the three drug release profiles comprises at least two different drugs.

14. The drug delivery device of claim 1, wherein the at least one drug released from the hydrogel during the three drug release profiles comprises three different drugs.

15. The drug delivery device of claim 14, wherein a first drug is selected from the group consisting of hemostatic agents, topical anesthetics, anti-adhesion agents, antibiotics, and combinations thereof; a second drug is selected from the group consisting of analgesics, anti-inflammatories, anti-adhesion agents, antibiotics, and combinations thereof; and a third drug is selected from the group consisting of anti-cancer agents, anti-scarring agents, proteins, and combinations thereof.

16. The drug delivery device of claim 1, wherein the first drug release profile is from about 2 days to about 8 days, the second drug release profile is from about 9 days to about 29 days, and the third drug release profile is from about 30 days to about 120 days.

17. The drug delivery device of claim 1, wherein the first drug release profile is determined by water solubility of the drug, the second drug release profile is determined by hydrolysis of the hydrogel, and the third drug release profile is determined by mass loss of the hydrogel.

18. A drug delivery device, comprising:
   at least one drug; and
   a biocompatible crosslinked polymer hydrogel comprising a backbone, and at least one biocompatible crosslinker region comprising a crosslinked synthetic crosslinker molecule with a pre-crosslinked molecular weight of less than about 2000, in combination with at least one biocompatible functional polymer region comprising a crosslinked synthetic polymer molecule with a pre-crosslinked molecular weight of more than about 7 times the molecular weight of the pre-crosslinked crosslinker molecule,
   wherein the biocompatible crosslinked polymer hydrogel comprises at least three drug release profiles comprising a first drug release profile of from about 0 days to about 10 days, a second drug release profile of from about 0 days to about 30 days, and a third drug release profile of from about 0 days to about 180 days, and wherein the at least one drug having the first drug release profile is incorporated into the crosslinked polymer hydrogel without binding, the at least one drug having said second drug release profile is incorporated into the crosslinked polymer hydrogel by a means selected from the group consisting of bound by a pendant linkage and incorporated into the backbone, and the at least one drug having said third drug release profile is incorporated into the crosslinked polymer hydrogel by a means selected from the group consisting of bound by a pendant linkage and incorporated into the backbone.

19. The drug delivery device of claim 18, wherein the biocompatible crosslinked polymer comprises at least three links between the crosslinker region and the functional polymer region, and the links are a reaction product of at least one electrophilic functional group with of at least one nucleophilic functional group that react to form the hydrogel, and wherein the biocompatible crosslinker region of the hydrogel has a solubility of at least 1 g/100 ml in an aqueous solution.

20. The drug delivery device of claim 18, wherein the biocompatible crosslinked polymer further comprises at least one biodegradable link.

21. The drug delivery device of claim 18, wherein the at least one drug released from the hydrogel during the three drug release profiles comprises three different drugs, comprising a first drug selected from the group consisting of hemostatic agents, topical anesthetics, anti-adhesion agents, antibiotics, and combinations thereof; a second drug selected from the group consisting of analgesics, anti-inflammatories, anti-adhesion agents, antibiotics, and combinations thereof; and a third drug selected from the group consisting of anti-cancer agents, anti-scarring agents, proteins, and combinations thereof.

22. The drug delivery device of claim 18, wherein the first drug release profile is from about 2 days to about 8 days, the second drug release profile is from about 9 days to about 29 days, and the third drug release profile is from about 30 days to about 120 days.

23. The drug delivery device of claim 18, wherein the first drug release profile is determined by water solubility of the drug, the second drug release profile is determined by hydrolysis of the hydrogel, and the third drug release profile is determined by mass loss of the hydrogel.

* * * * *